United States Patent
Mio et al.

[11] Patent Number: 5,890,894
[45] Date of Patent: Apr. 6, 1999

[54] IMPRESSION TRAY FOR FIXED DENTAL PROSTHESIS

[76] Inventors: Alessandro Mio, Via Campaner 3, 30020 Pradipozzo (VE); Alessandro Ivano Zaccheo, Via Pilacorte 1, 30026 Portogruaro (VE), both of Italy

[21] Appl. No.: 827,316

[22] Filed: Mar. 26, 1997

[30] Foreign Application Priority Data

Apr. 4, 1996 [IT] Italy .................................. TO96A0264

[51] Int. Cl.⁶ .................................................. A61C 9/00
[52] U.S. Cl. .................................................................. 433/37
[58] Field of Search ............................... 433/37, 38, 39, 433/42, 43, 47

[56] References Cited

U.S. PATENT DOCUMENTS

| 2,860,414 | 11/1958 | Brant | 433/43 |
| 4,003,132 | 1/1977 | Bech | 433/42 |
| 4,445,854 | 5/1984 | Bekey et al. | 433/42 X |
| 4,543,062 | 9/1985 | Lee | 433/42 X |
| 4,902,227 | 2/1990 | Smith | 433/42 X |

*Primary Examiner*—Nicholas D. Lucchesi
*Attorney, Agent, or Firm*—Herbert Dubno

[57] ABSTRACT

An impression tray for fixed dental prosthesis has a first and second opposed recesses containing the material to be impressed, through which both the impressions of the upper and lower side of the dental arcade of a patient can be taken simultaneously.

9 Claims, 3 Drawing Sheets

IMPRESSION TRAY FOR FIXED DENTAL PROSTHESIS

SPECIFICATION

FIELD OF THE INVENTION

The present invention refers to an impression tray for fixed dental prosthesis used in teeth treatment for cosmetic or functional reasons by, either through their capsulation or replacement of missing teeth.

BACKGROUND OF THE INVENTION

Impressions are obtained by means of impression trays having different configurations according to the kind of impression to be taken, i.e. suitable either for the impression of the complete upper or lower dental arcade or for a section of the upper or lower dental arcade.

The impression trays are generally made of metal, namely aluminium or stainless steel or plastic and have a "U"-shaped section. The impression trays are filled with plastic material, and then they are introduced into the mouth and pressed down on the dental arcade whose impression has to be taken. Thus the plastic material is impressed and takes the configuration of the dental arcade.

When the impression has to be taken for both the upper arcade and lower arcade two single separate impressions are needed with a consequent loss of time and the risk of jeopardizing their precision when coupling both parts together. Usually, the impression tray is maintained in position though a finger pressure by the patient or by the dentist till the plastic material filling it has set. However, such a method is not safe as the pressure exerted by the fingers is not steady over the whole impression tray during the setting time of the impressing material and not be strong enough so that the result of the operation may be jeopardized.

After the plastic material has set, the impression tray is removed from the patient's mouth by pulling it off the dental arcade with manual movements which, in turn may cause deformations to the impression, jeopardizing the subsequent work.

Moreover, to avoid that the plastic material may remain stuck to the dental wall when removing the impression tray, impression trays are provided with a set of holes arranged on several rows, both on the side walls and on the bottom of the "U"-shaped section, over the whole extension of the impression trays Thus, the plastic material in the impression tray exceeding the quantity required for the purposes of the impression can run out of the holes and cause a retention along with the impression tray.

Therefore, this method requires the use of more plastic material than actually needed for the impression alone, with consequent higher costs.

OBJECT OF THE INVENTION

It is the object of the present invention to provide an impression tray for fixed dental prosthesis to obviate in a simple and safe way to the problems related to the known impression trays.

SUMMARY OF THE INVENTION

To reach this purpose the object of the present invention to provide an, impression tray for fixed dental prosthesis according to the invention, characterized in that it has a first and a second opposed recesses to contain the material to be impressed, through which both the impressions of the upper and lower side of a patient's dental arcade can be taken simultaneously.

BRIEF DESCRIPTION OF THE DRAWINGS

The features and advantages of te impression tray according to the present invention will be apparent from the following description based on the annexed drawings, which are supplied only by way of a non limiting example, and wherein.

SPECIFIC DESCRIPTION

Figure 1:
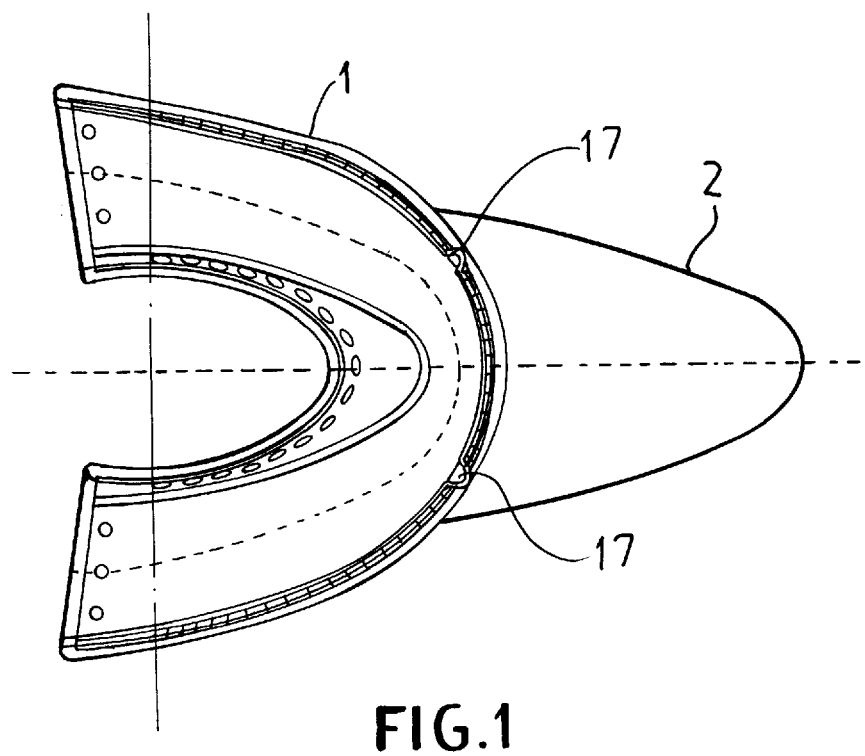
FIG. 1 is a plan view of an impression tray according to the present invention.

In FIG. 1, showing a plan view of an impression tray according to the present invention, reference number 1 indicates the impression tray, which in its plane position has substantially a "U" configuration following that of the dental arcade and consisting of both a buccal part and lingual part extending approximately to the retromolar trigone, whereas number 2 indicates a protruding part having a gripping function.

The "U" configuration thus obtained allows the patient to move the tongue, swallow and breathe adequately, with less inconvenience for the patient during the impression stage.

Figure 2:
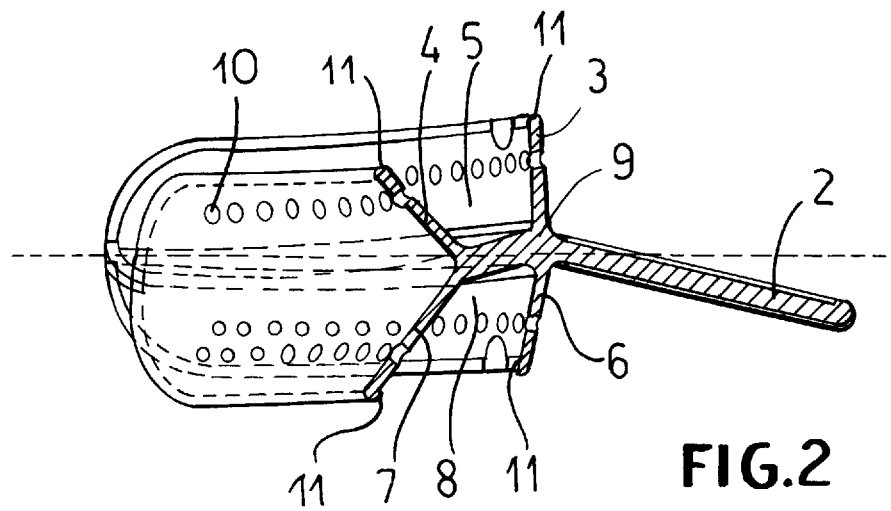
FIG. 2 is a lengthwise side section of an impression tray according to the present invention.

In FIG. 2 showing a lengthwise section of an impression tray 1 according to the present invention, numbers 3 and 4 indicate two walls, one outside and one inside to define laterally a substantially "U" -shaped recess 5 forming the upper part of the impression tray 1 following the upper dental arcade. Numbers 6 and 7 indicate two side walls, one outside and one inside to define laterally a substantially upturned "U"-shaped recess 8 forming the lower part of the impression tray 1 which follows the the lower dental arcade.

Therefore, the two recesses related to the upper and lower dental arcade respectively are opposed to each other.

Reference numeral 9 indicates a closing and joining wall for the opposed "U"-shaped recesses 5 and 8. The thickness of the wall 9 is not constant over the whole extension of the impression tray but varies from about 3 mm max. for the incisive area to about 1 mm min. in correspondence with the retromolar area, to comply with the closing angle of the mouth.

Also, the joining wall 9 is extending in compliance with the Spee's curve. Moreover, the width of the recesses 5 and 8 is not constant as it increases from the incisive area to the retromolar area to comply with the configuration of the dental arcade.

Outside walls 3 and 6 are inclined by about 3–4 degrees inwards the respective recesses 5 and 8 to follow the configuration of the dental arcade.

The height of the internal wall 4 with respect to the horizontal plane of the impression tray is lower than the height of the external wall 3, whereas the height of the internal wall 7 is higher than the external wall 6, in order to follow the configuration of the dental arcade.

Always in order to follow the shape of the dental arcade, the external or outside wall 3 has a height varying from a maximum value in the front section to a minimum value in the rear section of the impression tray where it ends with rounded corners.

Also the side wall 6, whose height is substantially constant, ends with rounded corners to avoid a contact with the mastication muscles.

Each side wall 3, 4, 6 and 7 is provided with a row of holes having about 1.5 mm diameter, indicated with number 10.

This row of holes 10 is located at a distance from the plane of wall 9, which is equal to about ⅔ of the height of the side walls.

A row of holes 10 is also obtained at the end of wall 9 in the retromolar area. At the end of the side walls 3, 4, 6 and 7 and over their whole extension a small tooth indicated by number 11 is provided, which is directed inside the recesses 5 and 8.

The holes 10 and the small tooth 11 have the function to anchor the impression tray to the plastic material and allow the removal of the impression tray after taking the impression and the consequent setting of the plastic material.

Number 2 indicates the handgrip of the impression tray, which is inclined downwards with respect to the horizontal plane of the impression tray. Thus, the impression tray can be easily removed from the mouth and obtain a more precise impression. In addition, said inclination reduces the friction of the patient's lips on the impression tray and will cause less inconvenience to the patient during the impression stage.

Figure 3:
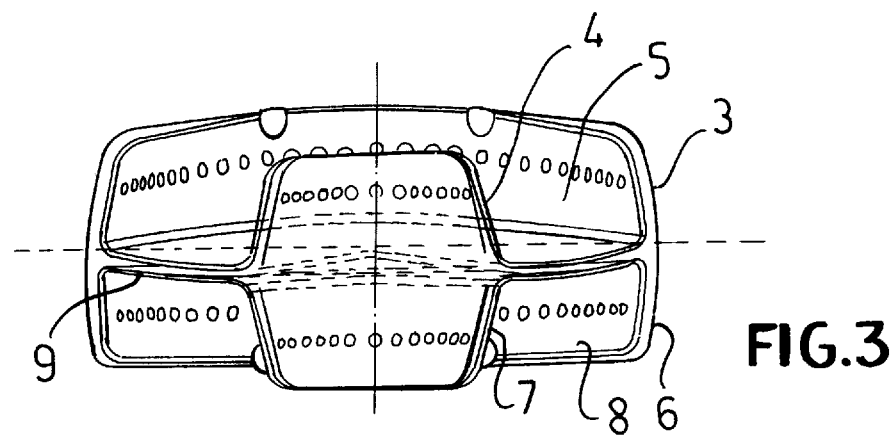
FIG. 3 is a rear view of an impression tray according to the present invention.

In FIG. 3, showing a front view of an impression tray according to the present invention, numbers 3 and 4 indicate the walls defining the upper recess 5 of the impression tray, whereas numbers 6 and 7 indicate the walls defining the lower recess 8 of the impression tray.

Number 9 indicates the common wall joining the recesses 5 and 8, whose inclination with respect to the horizontal plane of the impression tray determines an angle in compliance with the Wilson's curve.

Figure 4:
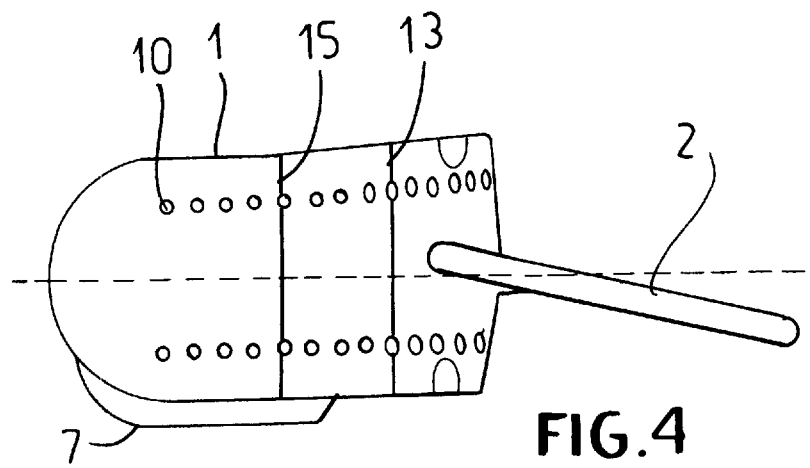
FIG. 4 is a side view of an impression tray according to the present invention.

In FIG. 4, showing a side view of an impression tray according to the present invention, number I indicates the impression tray, number 2 indicates the handgrip of the impression tray and number 10 indicates the anchoring holes of the impression tray to the plastic material used for the impression.

Number 13 indicates a reference notch to position the impression tray within the patient's mouth.

After filling the recesses 5 and 8 with the required quantity of plastic material, the impression tray is introduced into the patient's mouth; the patient will maintain it in position simply through the closing pressure of the mouth till the impressing material has set.

Thus, the obtained impression faithfully reflects both the upper and lower sections of the dental arcade in a natural closing position of the mouth. This will avoid any coupling errors that may arise when taking the two impressions separately, as done according to the known state of the art.

To remove the impression tray from the mouth and avoid possible deformations to the impression just taken due to the adhesion of plastic material to the dental arcade, air is blown between the plastic material of the impression and the dental arcade using the syringe of the dental unit.

In order to allow this operation (i.e. the syringe insertion), the side walls 3 and 6 have four small recesses, indicated by number 17, which are in correspondence of the teeth "23" and "13" (upper) and with the teeth "33" and "43" (lower); two of the recesses 17 are shown in FIG. 1, and the other two are symmetrically opposed recesses, not shown in FIG. 1, in line with the lower teeth.

Figure 5:
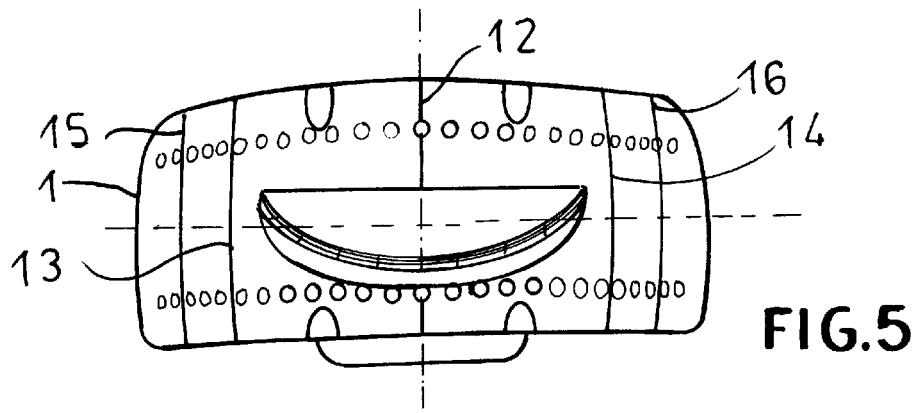
FIG. 5 is a front view of an impression tray according to the present invention.

To ensure a correct position of the impression tray on the dental arcades, the external side of the impression tray has some reference notches, as indicated by numbers 12, 13, 14, 15 and 16 in FIG. 5.

The notch 12 is located in correspondence with the central line of the dental arcade between the teeth "11"-"21" and "41"-"31", whereas the notches 13 and 14 are placed in correspondence with the side teeth "23"-"13" and "43"-"33" respectively.

The notches 15 and 16 are located in line with the teeth "16"-"26" and "36"-"46" respectively.

The notches 12, 13, 14, 15 and 16 can be provided either raised or in low relief. Both the way and use of the impression tray according to the present invention will be apparent from the above description and annexed drawings.

As it results from the above description, the impression tray for fixed prosthesis according to the present invention provides for the following advantages:

one single operation is enough to impress both the upper dental arcade and lower dental arcade, as both impressions are obtained simultaneously;

time saving for the patient and the dentist;

higher precision for the impression;

easy removal of the impression tray From the patient's mouth;

less inconvenience for the patient's lips;

less inconvenience for the patient to move the tongue, swallow and breathe;

the impression tray can be easily placed in its correct position.

It is obvious, without prejudice to the principle of the present invention, that many changes are possible to the manufacturing features of the impression tray described above by way of example without departing from the novelty spirit of the innovative idea, and it is also clear that in practical actuation of the invention the configurations and dimensions shown may differ from the ones described above and be replaced with technical equivalent elements.

Figure 7:
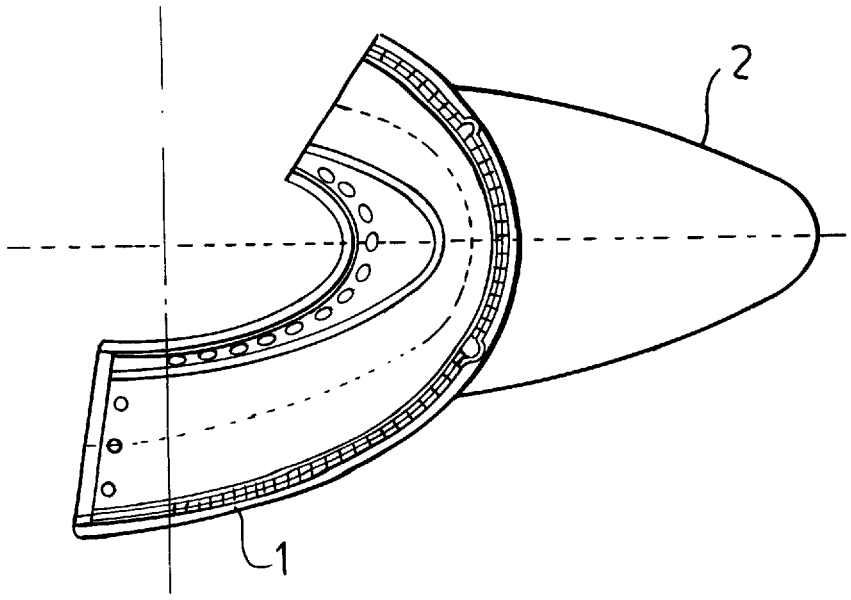
FIG. 7 is a plan view of still another embodiment of the impression tray according to the present invention.
Figure 6:
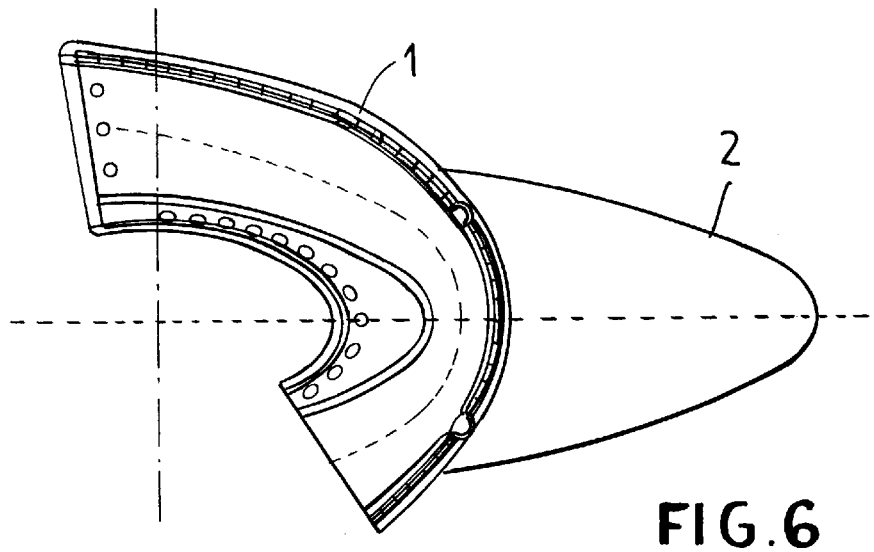
FIG. 6 is a plan view of an embodiment of the impression tray according to the present invention.
Figure 8:
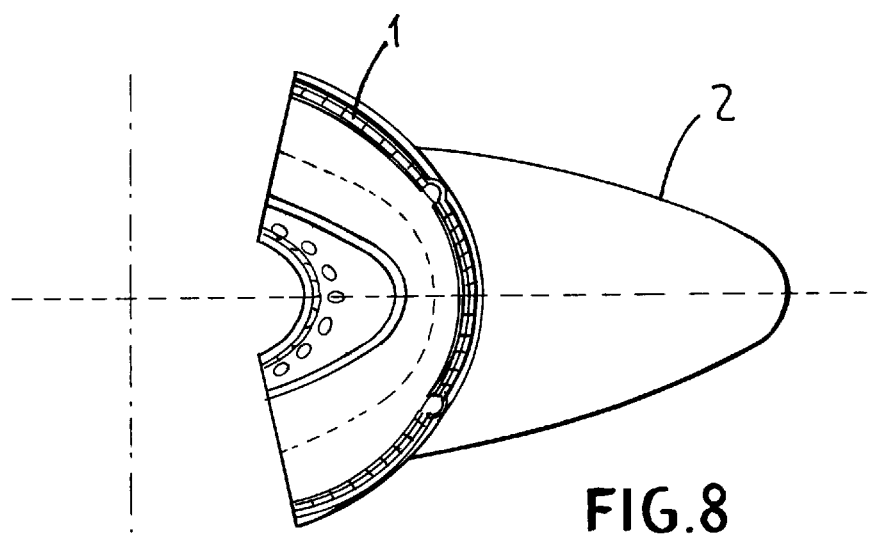
FIG. 8 is a plan view of yet another embodiment of the impression tray according to the present invention.

For instance, if only a section of the dental arcade has to be impressed, it is possible to change the configuration of the impression tray according to the illustration of FIGS. 6, 7 and 8, i.e, reducing the length of the right side or left side or of both sides, but leaving the other dimensions and features unchanged.

We claim:

1. A dental impression tray comprising:
a one-piece outer U-shaped continuous peripheral retaining wall defined between respective upper and lower edges;
a one-piece inner U-shaped continuous peripheral retaining wall defined between respective upper and lower edges and spaced inwardly from said peripheral outer wall; and
a dividing wall spaced inwardly from the respective upper and lower edges of said outer and inner peripheral walls and bridging the latter to form an upper and lower opposing recesses adapted to receive a material to be impressed for simultaneously obtaining registered upper and lower dental arcade impressions, said dividing wall being inclined with respect to the horizontal plane of the impression tray in accordance with the Spee and Wilson curves and having a variable thickness.

2. The impression tray defined in claim 1 wherein each of the upper and lower recesses has a respective width gradually increasing from the incisive area towards the retromolar area according to the configuration of the dental arcade.

3. The dental tray defined in claim 1 wherein said thickness changes from at most 3 mm in the vicinity of the incisive area and approximately 1 mm in the vicinity of the retromolar area.

4. The dental tray defined in claim 1 wherein said outer peripheral wall is inwardly concave and the inner peripheral wall is outwardly convex with respect to said recesses.

5. The dental tray defined in claim 1 wherein each of said inner and outer peripheral walls is provided with:

a plurality of respective rows of spaced apart holes extending longitudinally between the retromolar and incisive area and at a predetermined distance above and below from the dividing wall, and a plurality of teeth extending in generally vertical plane toward the opposite edge of the outer peripheral wall.

6. The dental tray defined in claim 1 wherein said outer peripheral wall is formed with a plurality of spaced apart reference notches and ribs extending between the upper and lower edges of the outer wall for a correct positioning of the impression tray.

7. The dental tray defined in claim 6 wherein the notches are aligned with the upper teeth "23" and "13" and the lower teeth "33" and "43" and are provided for receiving an air jet blown on between said wall and teeth to remove the impression tray.

8. The dental tray defined in claim 7 wherein said ribs are provided aligned with 11-21, 31-41, 23-43, 13-33, 16-26 and 36-46 pairs of teeth.

9. The impression tray defined in claim 1 further comprising a handgrip inclined with respect to a horizontal at angle of 3 to 4 degrees.

\* \* \* \* \*